United States Patent [19]
Knieler et al.

[11] Patent Number: 6,160,196
[45] Date of Patent: *Dec. 12, 2000

[54] ANTIMICROBIAL WOUND COVERINGS

[75] Inventors: Roland Knieler, Hamburg; Axel von Wolff, Handorf, both of Germany

[73] Assignee: Beiersdorf AG, Hamburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/910,441

[22] Filed: Aug. 5, 1997

[30] Foreign Application Priority Data

Aug. 6, 1996 [DE] Germany .............. 196 31 421

[51] Int. Cl.⁷ ..................... A61F 13/00
[52] U.S. Cl. ............... 602/48; 602/42; 602/44; 424/443; 424/447
[58] Field of Search ............... 602/48, 42, 44, 602/45, 43; 424/447, 443

[56] References Cited

U.S. PATENT DOCUMENTS

| | | |
|---|---|---|
| 4,035,146 | 7/1977 | Brenner et al. . |
| 4,929,498 | 5/1990 | Suskind et al. . |
| 4,990,144 | 2/1991 | Blott . |
| 5,147,338 | 9/1992 | Lang et al. . |
| 5,167,613 | 12/1992 | Karami et al. . |
| 5,322,695 | 6/1994 | Shah et al. . |
| 5,395,305 | 3/1995 | Koide et al. ............... 602/48 |
| 5,707,736 | 1/1998 | Levy et al. ............... 428/375 |
| 5,779,736 | 7/1998 | Frederick et al. . |
| 5,849,311 | 12/1998 | Suwan et al. . |

FOREIGN PATENT DOCUMENTS

| | | |
|---|---|---|
| 0 136 900 | 4/1985 | European Pat. Off. . |
| 0 255 248 | 2/1988 | European Pat. Off. . |
| 0 296 441 | 12/1988 | European Pat. Off. . |
| 0 328 421 | 8/1989 | European Pat. Off. . |
| 0 475 807 | 3/1992 | European Pat. Off. . |
| 0 691 133 | 1/1996 | European Pat. Off. . |
| 30 33 606 | 4/1982 | Germany . |
| 30 35 037 | 4/1982 | Germany . |
| 31 11 336 | 4/1982 | Germany . |
| 32 23 851 | 2/1984 | Germany . |
| 36 35 851 | 2/1988 | Germany . |
| 40 26 153 | 2/1992 | Germany . |
| 52 415 | 9/1990 | Sao Tome/Principe . |
| 2 202 150 | 9/1988 | United Kingdom . |
| 80/01041 | 5/1980 | WIPO . |
| 89/02754 | 4/1989 | WIPO . |

*Primary Examiner*—Kira M. Lewis
*Attorney, Agent, or Firm*—Norris, McLaughlin & Marcus, P.A.

[57] ABSTRACT

Wound covering which is characterized in that it is made of a hydrophobic bacteria-adsorbing material which comprises an antimicrobial active compound which is not released into the wound. It is preferably made of a mixture of hydrophobic fibres and fibres comprising the antimicrobial active compound.

10 Claims, No Drawings

ANTIMICROBIAL WOUND COVERINGS

The invention relates to wound coverings which can be employed for treatment of infected wounds or for preventive protection against wound infections.

Antimicrobial treatment of wounds or preventive treatment of wounds to protect them against infections by microorganisms have been known for a long time. The use of oxidizing agents (for example iodine tincture) or antiseptics (for example ointments comprising silver sulphadiazine) may be mentioned here by way of example. If oxidizing agents or other antimicrobial active compounds are employed in an extra pure form, in solution, as an ointment or in another presentation form, the action mechanism is always comparable. Microorganisms such as bacteria are indeed reliably destroyed. However, a number of disadvantages remain to be mentioned: Bacteria which have died remain in the wound. Wounds cannot be cleaned to remove the active compound reliably after the application, since it spreads in the entire wound. Finally, if these active compounds occur freely in the wound, they can also attack and destroy cells and substances in the wound fluid which promote wound healing (for example damage to healing-promoting protein substances by oxidizing agents).

One of the next steps in wound treatment was to cover wounds with antimicrobially treated wound coverings. These wound coverings can be prepared, for example, by treatment of carriers such as woven fabrics, nonwovens, gauze and the like with active compounds. By covering wounds with these products which do not release the active compound, however, as a rule only a protective function is achieved. The wound covering merely forms a barrier for microorganisms which are prevented from penetrating into the wound from the outside by being destroyed on contact with the product. The action in the wound is negligible here. It therefore cannot be regarded as treatment of an infected wound.

If the active compound is released from antimicrobially treated wound coverings into the wound, the same disadvantages arise as with application in an extra pure form, as a solution, as an ointment or in another presentation form. That is to say, the bacteria remain in the wound, no reliable cleaning of the wound is possible and troublesome effects may occur.

In addition to the two most widely used treatment methods described above, that is to say application of antimicrobial formulations and the use of impregnated wound treatment materials, the use of hydrophobized carrier materials is also described (EP-B 021 230, EP-B 162 026 and EP-A 296 441). In this case, hydrophobic bacteria are adsorbed by a wound covering, which has been hydrophobized by an involved chemical process, in a hydrophilic medium (water, salt solution or wound fluid). The bacteria are then withdrawn from the wound by removal of the wound covering. A decisive disadvantage here is that, in contrast to the customary treatment methods mentioned above, bacteria and microorganisms are not destroyed. This disadvantage is intensified further if the treated wound dries out. This means the loss of the hydrophilic medium, which contributes decisively to the interaction between the wound covering and bacteria. The bacteria and microorganisms which have not been destroyed become detached from the wound covering and fall back into the wound bed.

The object of the invention was therefore to develop a wound covering which does not have the disadvantages of the prior art and renders possible an improved treatment of infected wounds and/or protection against infections. This object is achieved by a wound covering according to claim 1.

By the combination according to the invention of a hydrophobic and therefore bacteria-adsorbing material and an antimicrobial active compound which is not released into the wound, a new action mechanism with a synergistic effect is achieved.

The wound covering serves as a barrier for microorganisms and it adsorbs the bacteria from the wound fluid. After the adsorption, these bacteria are destroyed on the wound covering, and the destroyed bacteria and unused active compound are likewise removed with the removal of the covering. They therefore no longer interfere with the healing process.

Suitable bacteria-adsorbing hydrophobic materials can be synthetic or naturally occurring or chemically modified naturally occurring polymers, such as polyethylene, polypropylene, polyurethane, polyamide, polyester, polyvinyl chloride, polytetrafluoroethylene or polymers which are prepared by covalent linking of hydrophilic substances with hydrophobic groups, for example according to EP-B 21 230. The bacteria-adsorbing properties of hydrophobic materials are known (cf. D. F. Gerson et al., Biochim. Biophys. Acta, 602 (1980, 506–510); Y. Fujioka-Hirai. et al., J. of Biochemical Materials Research, Volume 21, 913–20 (1987); S. Hjerten et al., J. of Chromatography 101 (1974), 281–288; M. Fletcher et al., Appl. and Environmental Microbiology, January 1979, 67–72). The hydrophobic properties can also be detected easily by a water drop test, in which the water beads on the material.

Suitable antimicrobial active compounds, which are primarily to be understood as meaning substances which are known per se, such as, for example, chlorhexidine or phenol derivatives, such as thymol and eugenol, or the chlorophenols or chlorodiphenyl ethers known in DE-PS 32 15 134, are distinguished by the fact that they adhere firmly to the wound covering, act on or in this on the microorganisms and are not released, or at least are not released noticeably, into the wound. This can be effected by physical incorporation into or addition onto suitable carriers, for example incorporation of hydrophobic active compounds into hydrophobic carrier materials or, for example, also by covalent bonding to these. The active compound/carrier systems should be distinguished by the fact that their antimicrobial activity is retained even during several extractions with aqueous solutions or wound fluid. The wound coverings should comprise the antimicrobial active compound in an amount of at least 0.001% by weight in order to achieve an adequate activity. This amount is preferably 0.1–10%, particularly preferably 0.1–2% by weight.

Although the antimicrobial active compounds adhere firmly to the wound covering, they should nevertheless not be toxic or irritating to the skin, in order to exclude any negative action on the patient.

The wound coverings according to the invention, which as a rule are in the form of more or less thin sheet-like structures, can be made of a hydrophobic material in the form of a woven fabric, knitted fabric, net, nonwoven, foam or a film, which comprises the antimicrobial active compound in or on it.

In another embodiment, they can be made of a nonwoven, woven fabric, knitted fabric or net with on the one hand hydrophobic fibres or threads and on the other hand fibres or threads which comprise the active compound. They can also be built up from mixed threads which are made of hydrophobic fibres and antimicrobially active fibres.

It is important here that the wound coverings overall have a significantly hydrophobic character.

In a preferred embodiment, the antimicrobial fibres are acetate fibres, which particularly preferably comprise a chlorinated phenoxy bactericide. Such fibres are commercially obtainable as MICROSAFE fibres.

Another possibility for building up the wound covering comprises bonding the hydrophobic fibres by a binder which comprises the antimicrobial agent.

The wound coverings should be permeable to air and water vapour. However, since they can absorb essentially no wound secretion per se, it may prove to be advantageous to render them more permeable, for example by perforation, and then to deposit an absorbent layer on them. In the case of wounds which must not dry out, so-called hydroactive wound dressings or wound dressings based on hydrogels can be positioned over the permeable wound covering.

To fix the coverings, these can also be bonded, for example, on the side facing away from the wound, to a projecting carrier material which has been given a self-adhesive treatment. The side facing the wound is then usually provided with a protective covering, for example of siliconized paper.

The antimicrobial wound coverings according to the invention—if appropriate combined with other materials as described—are cut or stamped into the desired formats, sealed and sterilized, depending on the envisaged intended use.

The following examples are intended to illustrate the invention by way of example.

EXAMPLE 1

A knitted fabric (a tricot warp knitted fabric with a weight per unit area of 170 g/m$^2$) is produced from a thread which is composed of polyester fibres to the extent of 80% and Microsafe AM® fibres to the extent of 20%. The knitted fabric is sterilized and employed as a wound covering under a hydroactive wound dressing (for example in accordance with WO 94/07935).

EXAMPLE 2

Polypropylene fibres are bonded to a nonwoven with Microsafe AM® fibres from Hoechst Celanese (thickness 0.5 mm, 50 g/m$^2$, 90% by weight of polypropylene fibres, 10% by weight of Microsafe AM® fibres). The nonwoven is used as a wound covering with a commercially available fixing.

EXAMPLE 3

A hydrophobic polyurethane film based on an aliphatic polyester-urethane is produced by a dispersion casting process (thickness 80 μm). By addition of an appropriate amount of thymol (2-isopropyl-5-methylphenol) to the aqueous dispersion, the film comprises 0.1% by weight of thymol. The film is perforated (diameter of the holes: 1 mm, perforated area 15%). The film is then sterilized and employed as a wound covering under a hydroactive wound dressing.

What is claimed is:

1. A wound covering comprising a hydrophobic, bacteria-absorbing synthetic or naturally-occurring polymeric fiber material, having adhered thereto an antimicrobial active compound which is adapted to not be released into the wound.

2. Wound covering according to claim 1, wherein the hydrophobic material is present in the form of a woven fabric, knitted fabric, net, or a nonwoven which comprises the antimicrobial active compound.

3. Wound covering according to claim 1, wherein, said material is a nonwoven, woven fabric, knitted fabric or net of hydrophobic fibers or threads and fibers or threads which comprise the antimicrobial active compound.

4. Wound covering according to claim 1, wherein said material is a nonwoven, woven fabric, knitted fabric or net with mixed threads of hydrophobic fibers which comprise the antimicrobial active compound.

5. Wound covering according to claim 3, wherein the fibers or threads comprising the antimicrobial active compound are acetate fibers or threads.

6. Wound covering according claim 1, wherein said wound covering is permeable to water.

7. Wound covering according to claim 6, in combination with an absorbent covering placed behind said wound covering.

8. Wound covering according to claim 6, in combination with a moisture-donating covering placed behind said wound covering.

9. Wound covering according to claim 1, wherein said wound covering is covered, on the side facing away from the wound, with a carrier material which projects beyond the wound covering and has been given a self-adhesive treatment.

10. The wound covering of claim 1, wherein said polymeric fiber is a fiber of a polymer selected from the group consisting of polyethylene, polypropylene, polyurethane, polyamide, polyester, polyvinyl chloride, polytetrafluoroethylene and polymers which are prepared by covalent linking of hydrophilic substances with hydrophobic groups.

* * * * *